United States Patent

Gallenkamp et al.

Patent Number: 4,568,760
Date of Patent: Feb. 4, 1986

[54] PROCESS FOR THE PREPARATION OF LACTIC ACID SILYL ESTERS

[75] Inventors: Bernd Gallenkamp, Wuppertal; Hermann D. Krall, Duesseldorf, both of Fed. Rep. of Germany

[73] Assignee: Bayer Aktiengesellschaft, Leverkusen, Fed. Rep. of Germany

[21] Appl. No.: 752,204

[22] Filed: Jul. 3, 1985

[30] Foreign Application Priority Data

Jul. 7, 1984 [DE] Fed. Rep. of Germany ....... 3425138
Feb. 27, 1985 [DE] Fed. Rep. of Germany ....... 3506839
May 18, 1985 [DE] Fed. Rep. of Germany ....... 3517947

[51] Int. Cl.$^4$ .......................... C07F 7/04; C07F 7/08; C07F 7/18
[52] U.S. Cl. .................................................. 556/440
[58] Field of Search ........................................ 556/440

[56] References Cited

U.S. PATENT DOCUMENTS 2,048,799  7/1936  Lawson .......................... 556/440 X
2,770,631  11/1956  Merker ............................. 556/440

Primary Examiner—Paul F. Shaver
Attorney, Agent, or Firm—Sprung, Horn, Kramer & Woods

[57] ABSTRACT

Novel lactic acid silyl esters of the formula

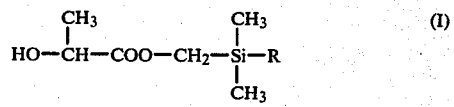

in which
R represents alkyl or aryl, are obtained by a new process which comprises reacting a lactic acid of the formula

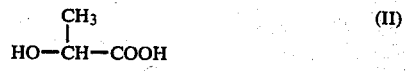

with a chloromethylsilane of the formula

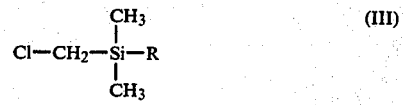

in which
R has the meaning indicated above, in the presence of a tertiary amine and, if appropriate, in the presence of an additional diluent, at temperatures between 50° and 120° C.

9 Claims, No Drawings

PROCESS FOR THE PREPARATION OF LACTIC ACID SILYL ESTERS

The present invention relates to a new process for the preparation of new lactic acid silyl esters and to their use as intermediates for the synthesis of compounds, which have herbicidal activity.

It is already known that 2-tosyloxypropionic acid (silyl-methyl)-esters can be used as intermediates for the synthesis of compounds having herbicidal activity (compare EP-OS (European Published Specification) No. 0,096,354, DE-OS (German Published Specification) No. 3,319,289 and EP-OS (European Published Specification) No. 0,095,115). It has also been disclosed that 2-tosyloxy-propionic(silyl-methyl)-ester is obtained, if 2-tosyloxypropionic acid halides are reacted with hydroxymethylsilyl derivatives. However, it is a disadvantage of this process that the compounds, which are required as starating materials, need to be prepared, in each case, in a two-stage reaction. Based on the starting materials used, the 2-tosyloxypropionic acid (silyl-methyl)-esters are obtained in a yield which is relatively low for practical purposes.

The present invention now provides a new process for the preparation of a lactic acid silyl ester of the formula

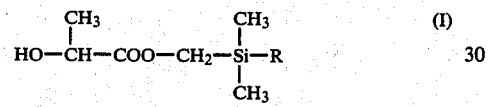

in which
R represents alkyl or aryl, which process comprises reacting a lactic acid of the formula

with a chloromethylsilane of the formula

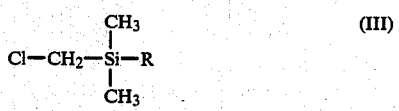

in which
R has the meaning indicated above, in the presence of a tertiary amine and, if appropriate, in the presence of an additional diluent, at temperatures between 50° and 120° C.

It has also been found that the lactic acid silyl esters of the formula (I) according to the invention are very useful as intemediates for the synthesis of compounds having herbicidal activity.

It must be denoted extremely surprising that lactic acid silyl esters of the formula (I) can be prepared by the process according to the invention in excellent purity and very high yields. In particular, it was not to be expected on the basis of the known state of art that the reaction does not take place at the hydroxy group but takes place at the carboxy group with high selectivity.

The process according to the invention has a number of advantages. Thus, the reaction components are accessible in a larger amount and are also to manipulate on an industrial scale without problems. The apparative expense required for carrying out the process is also low, and the working up of the reaction mixture that is obtained after the reaction is finished presents no difficulties. Further, simple acid binding agents are required only and, if at all, customary diluents are needed only. However, in particular the lactic acid silyl esters of the formula (I) can be prepared by the process according to the invention not only in very high yields but also free from undesired side products. Moreover, by the preparation of lactic acid silyl esters of the formula (I) by the process according to the invention, there are provided products from which 2-tosyloxy-propionic acid (silyl-methyl)-esters, which are important as intermediates for the synthesis of herbicides, can be prepared in an easier manner than by the known processes.

If the S enantiomer of lactic acid and chloromethyl-trimethyl-silane are used as starting substances and N,N-dimethyl-cyclohexylamine is used as a tertiary amine, then the course of the process according to the invention can be illustrated by the following formula scheme:

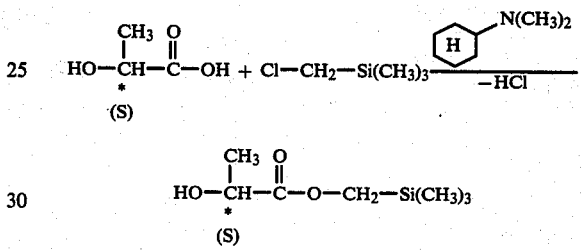

In the formulae above and also in the following description, the asymmetrically substituted carbon atom, in each case, is marked by a (*) if optically active compounds are concerned. The symbol "S" or "R" denotes the absolute configuration at the asymmetrically substituted carbon atom.

Formula (II) provides an unambiguous definition of the lactic acid required as starting substance in the process according to the invention. There can be used racemic lactic acid as well as optically active lactic acid. The use of the S-enantiomer of the lactic acid is particularly preferred. The racemic lactic acid and also the two optically active forms of the lactic acid are known.

Formula (III) provides a definition of the chloromethylsilanes which are also required as starting materials in the process according to the invention. In this formula, R preferably denotes alkyl with 1 to 4 or 12 carbon atoms or represents phenyl.

The following compounds may be mentioned as examples of chloromethylsilanes of the formula (III):
chloromethyl-trimethylsilane,
chloromethyl-dimethyl-ethyl-silane,
chloromethyl-dimethyl-n-propyl-silane,
chloromethyl-dimethyl-n-butyl-silane,
chloromethyl-dimethyl-n-dodecyl-silane,
chloromethyl-dimethyl-phenyl-silane.

The chloromethylsilanes of the formula (III) are known synthones in organic chemistry.

All the customary aliphatic, aromatic and heterocyclic tertiary amines can be used as bases, which act as acid binding agents in the process according to the invention. These include, preferably, triethylamine, tri-n-butylamine, benzyl-dimethylamine, N,N-dimethyl-cyclohexylamine, methyl-di-cyclohexyl-amine, pyridine, α-picoline, β-picoline, γ-picoline, methyl-dibenzyl-amine, 1,5-diaza-bicyclo-[4.3.0]-non-5-ene and 1,8-diaza-bicyclo[5.4.0]-undec-7-ene, N,N-Dimethylcyclohexylamine is particularly preferred.

All customary inert organic solvents can be used in the process according to the invention. Preferred are aromatic hydrocarbons, such as toluene and xylene, further ketones, such as acetone and methyl-isobutylketone, and also nitriles, such as acetonitrile. However, it is also possible to work in absence of additional organic solvents if the silyl compound is used in a sufficient excess.

The reaction temperatures can be varied within a certain range in the process according to the invention. In general, the reaction is carried out at temperatures between 60° C. and 110° C.

The process according to the invention is in general carried out under normal pressure. However, it is also possible to carry out the reaction under increased or reduced pressure.

In carrying out the process according to the invention, in general 1 to 4 moles, preferably 1.5 to 3 moles, of chloromethylsilane of the formula (III) as well as 1 to 3 moles, preferably 1.1 to 2 moles, of tertiary amine are employed per 1 mole of lactic acid of the formula (II). In general, a procedure is followed in which the tertiary amine is added to a mixture of the reaction components of the formula (II) and (III), if appropriate in an organic solvent. However, it is also possible to bring the components together in another sequence. Thereafter, the reaction mixture is heated to the temperature, which is desired in each case, for 10 to 15 hours. The subsequent working up is carried out by customary methods. In general, a procedure is followed in which the reaction mixture is cooled and added to diluted aqueous acid, then the phases are separated, the organic phase is washed with water several times and then subjected to a fractionated distillation under reduced pressure. The chloromethylsilane which has been used in excess is thereby recovered in pure form and can be used for further reactions. The lactic acid silyl esters which can be prepared by the process according to the invention are obtained in the form of colourless substances; a supplemental purification is not required in general.

If optically active lactic acid is used as starting substance in carrying out the process according to the invention, optically active lactic acid silyl ester is obtained. The configuration at the asymmetrically substituted carbon atom is retained in the course of the reaction. Accordingly, if the S-enantiomer of lactic acid is used, in each case, the corresponding S-enantiomer of the lactic acid silyl ester is formed.

The lactic acid silyl esters of the formula (I) have not been discovered until now. Thus, the present invention provides, as new compounds, a lactic acid silyl ester of the formula

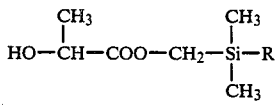

in which
R represents alkyl or aryl.

Preferred compounds of the formula (I) are those, in which R represents alkyl with 1 to 4 carbon atoms or with 12 carbon atoms or represents phenyl. Particularly preferred are the S-enantiomers of the lactic acid silyl esters of the formula

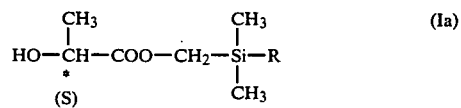

in which R has the meanings which have already been mentioned as preferred for this radical.

The lactic acid silyl esters of the formula (I) are valuable intermediates for the synthesis of compounds which have herbicidal properties. Thus, herbicidally active phenoxypropionic derivatives of the formula

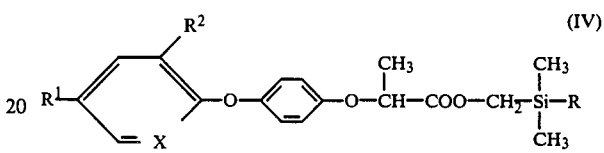

in which
R has the above-mentioned meaning,
$R^1$ represents chlorine or trifluoromethyl,
$R^2$ represents hydrogen or chlorine and
X represents nitrogen, a CH-group or a CCl-group,
can be prepared, if in a first stage lactic acid silyl esters of the formula

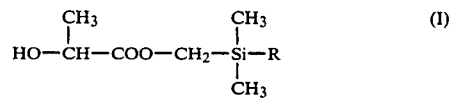

in which
R has the above-mentioned meaning, are reacted with tosylchloride in the presence of an acid binding agent, such as pyridine, and, if appropriate, in the presence of an additional diluent, at temperatures between 0° C. and 20° C., and in a second stage, the resulting 2-tosyloxypropionic acid (silyl-methyl)-esters of the formula

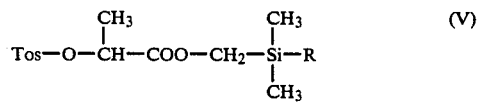

in which
R has the above-mentioned meaning and
Tos represents tosyl, are reacted with phenol derivatives of the formula

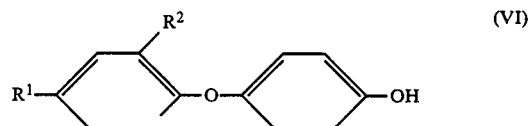

in which
$R^1$, $R^2$ and X have the above-mentioned meaning, in the presence of an acid binding agent and in the presence of a diluent, at temperatures between 50° C. and 120° C.

If for instance the S-enantiomer of the lactic acid (trimethylsilyl)-methylester and tosylchloride are used as starting substances and 4-(3,5-dichloropyridyl-2-oxy)phenol is used as reaction component, the course of the above mentioned process can be illustrated by the following formula scheme:

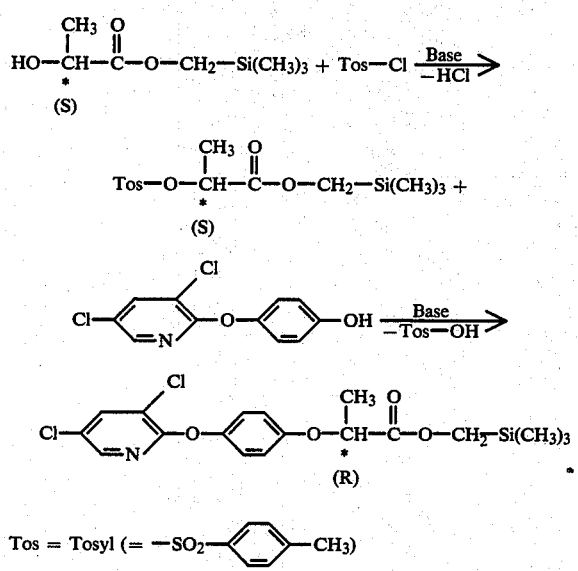

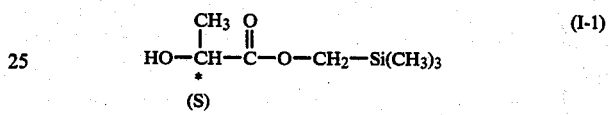

The phenol derivatives of the formula (VI) which are required as reaction components in carrying out the above-mentioned process for the preparation of phenoxy-propionic acid derivatives of the formula (IV) are known (compare DE-PS (German Patent Specification) No. 2,546,251).

Potassium carbonate and sodium carbonate can preferably be used as acid binding agents in the second stage of the above-mentioned process.

Polar inert organic solvents can preferably be used as diluents in the second stage of the above-mentioned process. Particularly preferred are ketones, such as acetone and methyl-isobutyl-ketone, further acetontrile and dimethylformamide.

The reaction temperatures can be varied within a certain range in the second stage of the above-mentioned process. In general, the reaction is carried out at temperatures between 50° C. and 120° C., preferably between 60° C. and 100° C.

The above-mentioned process for the preparation of phenoxypropionic acid derivatives of the formula (IV) is, in the first as well as in the second stage, in general carried out under normal pressure. However, it is also possible to carry it out under increased or reduced pressure.

In carrying out the second stage of the above-mentioned process for the preparation of phenoxypropionic acid derivatives of the formula (IV), an equivalent amount or a slight excess of a 2-tosyloxy-propionic acid (silyl-methyl)-ester of the formula (V) as well as 1.5 to 2.5 equivalents of acid binding agent and, if appropriate, anhydrous calcium sulphate are employed per 1 mole of phenol derivative of the formula (VI). The reaction components are, in each case, stirred in the solvent for several hours at the temperature required in each case. Working up is carried out by customary methods. In general, a procedure is followed in which the reaction mixture is filtered with suction and concentrated, the remaining residue is dissolved in an organic solvent, the resulting organic phase is washed successively with diluted aqueous alkali metal hydroxide solution and water, then dried and concentrated. The resulting residue is purified from volatile components, which still are contained, by short time heating under high vacuum ("incipient distillation").

If it is desired to prepare the R-enantiomer of a phenoxypropionic acid derivative of the formula (IV) by the above-mentioned process, it is required to use the S-enantiomer of a lactic acid silyl ester of the formula (I) as in the course of the reaction (in the second stage) a Walden inversion occurs at the asymmetrically substituted carbon atom. In analogous manner, the R-enantiomers of lactic acid silyl esters of the formula (I) must be used in each case to synthesise the S-enantiomers of phenoxypropionic acid derivatives of the formula (IV).

The following examples illustrate carrying out the process according to the invention and the preparation of phenoxypropionic acid derivatives of the formula (IV) starting from lactic acid silyl esters of the formula (I) according to the invention.

EXAMPLE 1

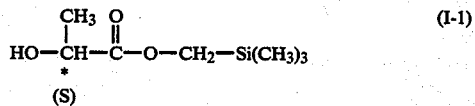

61.25 g (0.5 mole) of chloromethyltrimethylsilane were dropped into a mixture of 48.9 g ( 0.5 mole) of the S-enantiomer of the lactic acid, 78.9 g of 1.8-diaza-bicyclo[5.4.0]-undec-7-ene and 300 ml of methyl-iso-butylketone, whilst stirring, at a temperature of 80° to 90° C. The reaction mixture was stirred for a further 16 hours at 80° to 90° C., then it was cooled and washed with water. The organic phase was separated, dried and concentrated under reduced pressure. The remaining residue was released from remainders of volatile components by short time heating to 50° C. (bath temperature) under a pressure of 20 mbar and then was distillated. 52 g of a product (boiling point: 80°-82° C./15 mbar) were obtained, which consisted of 94% of the S-enantiomer of the 2-hydroxy-propionic acid (trimethylsilyl)-methylester. A yield of 55% of theory was calculated from this.

EXAMPLE 2

$$HO-\overset{CH_3}{\underset{*}{CH}}-\overset{O}{\overset{\|}{C}}-O-CH_2-Si(CH_3)_3 \quad (I-1)$$

(S)

400 g (3.15 moles) of N,N-dimethylcyclohexylamine were dropped into a mixture of 270 g (3 moles) of the S-enantiomer of the lactic acid and 736 g (6 moles) of chloromethyl-trimethyl silane within one hour, whilst stirring at room temperature without external cooling. The reaction mixture was heated to 95° C. with stirring and was kept at this temperature for 12 hours. Then the reaction mixture was cooled to room temperature and was poured into 1.2 liters of 10%-ic aqueous sulphuric acid. The organic phase was separated, washed twice with, in each case, 500 ml of water and was subjected to a fractionated distillation under reduced pressure. 430 g of a distillate were obtained thereby in a first fraction (boiling point: 50° C./20 mbar), which consisted of 15 g of an aqueous phase and of 415 g (3.38 moles) of chloromethyl-trimethylsilane. 371 g (2.10 moles) of the S-enantiomer of the 2-hydroxypropionic acid (trimethylsilyl)-methylester of a purity of 99.5% were obtained in a second fraction at a boiling point of b.p.=40° C./0.1 mbar. Based on chloromethyl-trimethyl-silane which had reacted, a yield of 85.1% of theory was calculated from this.

EXAMPLE 3

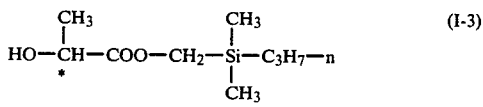
(I-3)

12.7 of N,N-dimethyl-cyclohexylamine were dropped into 9.8 g (0.1 mole) of the S-enantiomer of the lactic acid and 30 g of chloromethyl-dimethyl-n-propyl-silane at room temperature with stirring. The reaction mixture was heated to 100° C. for 16 hours. After cooling the reaction mixture to room temperature 50 ml of diethylether were added, the precipitate which deposited was filtered with suction, the filtrate was concentrated under reduced pressure and the remaining residue was distillated under reduced pressure. 11.7 g (54.2% of theory) of S-enantiomer of the 2-hydroxypropionic acid (dimethyl-n-propyl-silyl)-methylester of a purity of 90% were obtained in this manner. Boiling point: 105°–108° C./18.6 mbar.

EXAMPLE 4

Preparation of the R-enantiomer of the 2-[4-(3,5-dichloropyridyl-2-oxy)-phenoxy]-propionic acid (trimethylsilyl)-methylester;

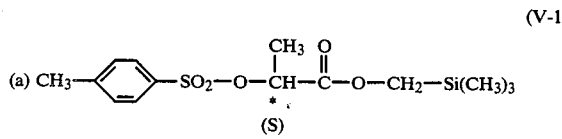
(V-1)

708 g (4 moles) of the S-enantiomer of the 2-hydroxypropionic acid (trimethylsilyl)-methylester were added to a solution of 916 g (4.8 moles) of tosylchloride in 800 g of pyridine at 0° C., and then the reaction mixture was stirred at 0° C. to 5° C. for a further 25 hours. Subsequently, 100 g of water were added, the reaction mixture was stirred for a further 2 hours at 5° C. to 10° C., and after adding 1,600 g of water and 2,000 g of toluene and after separating the phases, there was obtained an organic phase, which was washed twice with in total 3,000 g of 10%-ic aqueous sulphuric acid and then was washed twice with in total 3,000 g of water. After removing the toluene by distillation, 1,240 g of an oil remained, which consisted of 96% (corresponding to 3.6 mole) of the S-enantiomer of the 2-tosyloxypropionic acid (trimethylsilyl)-methylester. Based on the S-enantiomer of the 2-hydroxypropionic acid (trimethylsilyl)-methylester used as starting substance, the achieved yield was calculated as 90% of theory. Based on the content of 1% of the R-enantiomer of the compound of the formula (IV) in the reaction product, the S/R-ratio was calculated as 99:1.

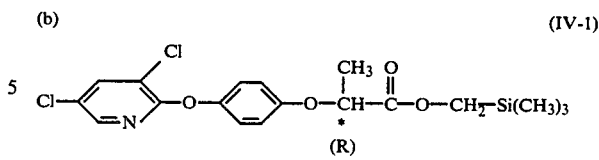
(IV-1)

A suspension of 930 g (3.45 moles) of 4-(3,5-dichloropyridyl-2-oxy)-phenol, 1,115 g (3.24 moles) of 2-tosyloxypropionic acid (trimethylsilyl)-methylester (content: 99% of S-enantiomer; 1% of R-enantiomer) and 925 g potassium carbonate in 5,100 g of acetonitrile was heated under reflux for 15 hours. After cooling to room temperature the reaction mixture was filtered. Subsequently, the acetonitrile was removed from the filtrate by distillation. The liquid raw product thus obtained was diluted with 3,500 g of toluene, then was washed twice with in total 1,500 g of 5%-ic aqueous sodium hydroxide solution, and was washed once with 1,000 g of 1%-ic aqueous sulphuric acid and once with 500 g of water. After removal of the toluene by distillation, there remained 1,360 g of a light oil which consisted of 85.7% (2.81 mole) of the R-enantiomer of the 2-[4-(3,5-dichloropyridyl-2-oxy)-phenoxy]-propionic acid (trimethylsilyl)-methylester of the formula (IV-1) and of 7.5% of the S-enantiomer of the compound of the formula (IV-1). The R/S-ratio is 92:8 and, based on the S-enantiomer of the 2-tosyloxypropionic acid (trimethylsilyl)-methylester used as starting substance, the yield is 86.8% of theory.

COMPARISON EXAMPLE

Preparation of the R-enantiomer of the 2-[4-(3,5-dichloropyridyl-2-oxy)-phenoxy]-propionic acid (trimethylsilyl)-methylester by a known process:

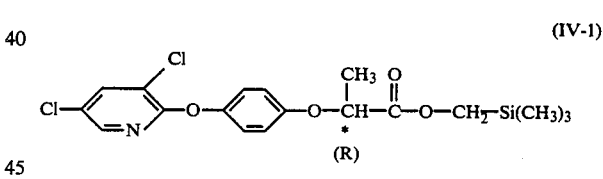
(IV-1)

4.9 g (0.03 mole) of 1,8-diaza-bicyclo[5.4.0]-undec-7-ene were added to a solution of 8.2 g (0.025 mole) of 2-[4-(3,3-dichloropyridyl-2-oxy)-phenoxy]-propionic acid in 50 ml of acetone, whilst stirring, at 20° C. The reaction mixture was stirred for a further 30 minutes at room temperature, and then 3.7 g (0.03 mole) of chloromethyl-trimethylsilane were added at room temperature as well. The reaction mixture was heated under reflux for 23 hours, then again 0.5 g of 1,8-diaza-bicyclo[5.4.0]-undec-7-ene and 0.8 g of chloromethyl-trimethylsilane were added, it was refluxed for another 23 hours, then the reaction mixture was cooled and the solvent was evaporated under reduced pressure. The remaining residue was dissolved in methylenechloride, and the resulting organic phase was successively washed with aqueous sodium hydroxide solution, diluted aqueous hydrochloric acid and water, and after drying the organic phase was concentrated. The remaining residue was released from remainders of volatile components by short time heating at 80° C. (bath temperature) under a pressure of 2 mbar. 2.5 g (24.2% of theory) of the R-enantiomer of the 2[4-(3,5- dichloropyridyl-2-oxy]-phenoxy]-propionic acid (trimethylsilyl)methylester were obtained in this manner.

Refractive index: $n_D^{23.5} = 1.5433$

Angle of rotation: $[\alpha]_D^{24} = +15.4°$ (1-molar solution in chloroform; cell length 10 cm).

It will be understood that the specification and examples are illustrative but not limitative of the present invention and that other embodiments within the spirit and scope of the invention will suggest themselves to those skilled in the art.

What is claimed is:

1. A process for the preparation of a lactic acid silyl ester of the formula

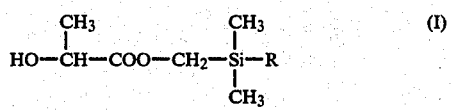

in which
R represents alkyl or aryl, which process comprises reacting a lactic acid of the formula

with a chloromethylsilane of the formula

in which
R has the meaning indicated above, in the presence of a tertiary amine and, if appropriate, in the presence of an additional diluent, at temperatures between 50° and 120° C.

2. A process as claimed in claim 1, wherein the S-enantiomer of the lactic acid of the formula (II) is employed as a starting substance.

3. A process as claimed in claim 1, wherein the chloromethylsilane is a compound of the formula (III), in which R is alkyl with 1 to 4 or 12 carbon atoms or is phenyl.

4. A process as claimed in claim 1, wherein the tertiary amine is N,N-dimethylcyclohexylamine.

5. A process as claimed in claim 1, wherein the reaction is carried out at a temperature between 60° C. and 110° C.

6. A process as claimed in claim 1, wherein 1 to 4 moles of a chloromethylsilane of the formula (III) and 1 to 3 moles of the tertiary amine are employed per 1 mole of lactic acid of the formula (II).

7. A lactic acid silyl ester of the formula

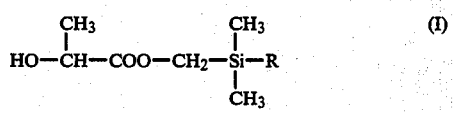

in which
R is alkyl or aryl.

8. A lactic acid silyl ester as claimed in claim 7, wherein R is alkyl with 1 to 4 or 12 carbon atoms or is phenyl.

9. A lactic acid silyl ester as claimed in claim 7, designated by the formula

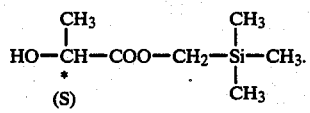

* * * * *